United States Patent
Barker et al.

(10) Patent No.: US 6,280,442 B1
(45) Date of Patent: Aug. 28, 2001

(54) MULTI-AXIAL BONE SCREW ASSEMBLY

(75) Inventors: B. Thomas Barker, Bartlett; John Stewart Young; Craig Squires, both of Memphis, all of TN (US); David Brumfield, Southaven, MS (US); Chris Johnson, Germantown; Dennis J. Buchanan, Memphis, both of TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/387,991

(22) Filed: Sep. 1, 1999

(51) Int. Cl.$^7$ .............................. A61B 17/68; A61B 17/70
(52) U.S. Cl. ................................................ 606/60; 606/61
(58) Field of Search ................... 606/60, 61, 69, 606/72, 73

(56) References Cited

U.S. PATENT DOCUMENTS

| | | |
|---|---|---|
| 4,763,644 | 8/1988 | Webb . |
| 4,805,602 | 2/1989 | Puno et al. . |
| 4,946,458 | 8/1990 | Harms et al. . |
| 5,005,562 | 4/1991 | Cotrel . |
| 5,176,678 * | 1/1993 | Tsou ........................ 606/61 |
| 5,207,678 | 5/1993 | Harms et al. . |
| 5,217,497 * | 6/1993 | Mehdian ..................... 623/17 |
| 5,261,909 | 11/1993 | Sutterlin et al. . |
| 5,360,431 | 11/1994 | Puno et al. . |
| 5,443,467 | 8/1995 | Biedermann et al. . |
| 5,466,237 | 11/1995 | Byrd III, et al. . |
| 5,474,555 | 12/1995 | Puno et al. . |
| 5,476,464 | 12/1995 | Metz-Stavenhagen et al. . |
| 5,501,684 | 3/1996 | Schlapfer et al. . |
| 5,520,690 | 5/1996 | Errico et al. . |
| 5,531,746 | 7/1996 | Errico et al. . |
| 5,549,608 | 8/1996 | Errico et al. . |
| 5,554,157 | 9/1996 | Errico et al. . |
| 5,562,661 | 10/1996 | Yoshimi et al. . |
| 5,575,792 | 11/1996 | Errico et al. . |

(List continued on next page.)

FOREIGN PATENT DOCUMENTS

| | | |
|---|---|---|
| 3711013 * | 9/1988 | (DE) . |
| 195 09 332 | 8/1996 | (DE) . |
| 2 173 104 | 10/1996 | (GB) . |

OTHER PUBLICATIONS

Protest under 37 C.F.R. Section 1.291, dated Mar. 3, 1997.
Declaration of J.P. Errico Pursuant To Protest Under 37 C.F.R. Section 1.291.
Sofamor Danek Meeting May 2, 1996, entitled Implemedics.

Primary Examiner—Paul J. Hirsch
Assistant Examiner—Michael B. Priddy
(74) Attorney, Agent, or Firm—Woodard, Emhardt, Naughton, Moriarty & McNett

(57) ABSTRACT

A bottom-loading multi-axial bone anchor apparatus is disclosed. The apparatus includes a receiver member, a crown member, a bone anchor and a retaining member. The receiver member defines an upper opening and a lower opening, which may form part of the same opening, a channel, and a groove. The crown member and bone anchor are loaded into the lower opening of the receiver member, and the retaining member fits around the bone anchor and into the groove in the receiver member. The bone anchor is capable of multi-axial positioning with respect to the receiver member. An elongated member is placed in the channel of the receiver member, contacting the crown member, and a compression member is applied via the upper opening. The compression member presses down on the elongated member, which presses down on the crown member and locks the bone anchor between the crown member and the retaining member.

43 Claims, 6 Drawing Sheets

U.S. PATENT DOCUMENTS

| | | |
|---|---|---|
| 5,578,033 | 11/1996 | Errico et al. . |
| 5,584,834 | 12/1996 | Errico et al. . |
| 5,586,984 | 12/1996 | Errico et al. . |
| 5,607,426 | 3/1997 | Ralph et al. . |
| 5,609,593 | 3/1997 | Errico et al. . |
| 5,609,594 | 3/1997 | Errico et al. . |
| 5,647,873 | 7/1997 | Errico et al. . |
| 5,669,911 | 9/1997 | Errico et al. . |
| 5,672,176 | 9/1997 | Biedermann et al. . |
| 5,688,273 | 11/1997 | Errico et al. . |
| 5,690,630 | 11/1997 | Errico et al. . |
| 5,733,286 | 3/1998 | Errico et al. . |
| 5,782,833 * | 7/1998 | Haider .................................... 606/61 |
| 5,797,911 * | 8/1998 | Sherman et al. ....................... 606/61 |
| 5,817,094 | 10/1998 | Errico et al. . |
| 5,879,350 * | 3/1999 | Sherman et al. ....................... 606/61 |
| 5,882,350 * | 3/1999 | Ralph et al. ........................... 606/61 |
| 5,885,286 * | 3/1999 | Sherman et al. ....................... 606/61 |
| 5,891,145 * | 4/1999 | Morrison et al. ...................... 606/61 |
| 6,053,917 * | 4/2000 | Sherman et al. ....................... 606/61 |
| 6,063,090 * | 2/2000 | Schlapfer .............................. 606/61 |

* cited by examiner

MULTI-AXIAL BONE SCREW ASSEMBLY

FIELD OF THE INVENTION

The present invention relates to devices and implants used in osteosynthesis and other orthopedic surgical procedures. Specifically, the present invention contemplates a bottom loading bone anchor assembly capable of achieving multiple angular orientations with respect to an elongated member extending along bone tissue.

BACKGROUND OF THE INVENTION

Several techniques and systems have been developed for correcting and stabilizing damage or malformation of bones, especially the long bones and the spine. In one type of system, an elongated member such as a bendable rod is disposed longitudinally along a length of the bone(s). In spinal applications, the rod is preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along a length of the spinal column by way of a number of fixation elements. A variety of fixation elements can be provided which are configured to engage specific portions of the vertebra and other bones. For instance, one such fixation element is a hook that is configured to engage the laminae of the vertebra. Another very prevalent fixation element is a screw that can be threaded into various parts of the vertebrae or other bones.

In one typical spinal procedure utilizing a bendable rod, the rod is situated on opposite sides of the spine or spinous processes. A plurality of bone screws are threaded into a portion of several vertebral bodies, very frequently into the pedicles of these vertebrae. The rods are affixed to these plurality of bone screws to apply corrective and stabilizing forces to the spine.

One example of a rod-type spinal fixation system is the TSRH® Spinal System sold by Medtronic Sofamor Danek, Inc. The TSRH® System includes elongated rods and a variety of hooks, screws and bolts all configured to create a segmental construct throughout the spine. In one aspect of the TSRH® System, the spinal rod is connected to the various vertebral fixation elements by way of an eyebolt. In this configuration, the fixation elements are engaged to the spinal rod laterally adjacent to the rod. In another aspect of the TSRH® System, a variable angle screw is engaged to the spinal rod by way of an eyebolt. The variable angle screw allows pivoting of the bone screw in a single plane parallel to the plane of the spinal rod. Details of this variable angle screw can be found in U.S. Pat. No. 5,261,909 to Sutterlin et al., owned by the Assignee of the present invention. One goal achieved by the TSRH® System is that the surgeon can apply vertebral fixation elements, such as a spinal hook or a bone screw, to the spine in appropriate anatomic positions. The TSRH® System also allows the surgeon to easily engage a bent spinal rod to each of the fixation elements for final tightening.

Another rod-type fixation system is the Cotrel-Dubosset/ CD® Spinal System sold by Medtronic Sofamor Danek, Inc. Like the TSRH® System, the CD® System provides a variety of fixation elements for engagement between an elongated rod and the spine. In one aspect of the CD® System, the fixation elements themselves include a body that defines a slot within which the spinal rod is received. The slot includes a threaded bore into which a threaded plug is engaged to clamp the rod within the body of the fixation element. The CD® System includes hooks and bone screws with this "open-back" configuration. Details of this technology can be found in U.S. Pat. No. 5,005,562 to Cotrel. One benefit of this feature of the CD® System is that the fixation element is positioned directly beneath the elongated rod. This helps reduce the overall bulkiness of the implant construct and minimizes the trauma to surrounding tissue.

On the other hand, these fixation elements of the CD® System are capable only of pivoting about the spinal rod to achieve variable angular positions relative to the rod. While this limited range of relative angular positioning is acceptable for many spinal pathologies, many other cases require more creative orientation of a bone screw, for instance, relative to a spinal rod. Certain aspects of this problem are addressed by the variable angle screw of the TSRH® System, as discussed in the '909 Patent. However, there is a need for a bone screw that is capable of angular orientation in multiple planes relative to the spinal rod. Preferably, the bone screw is capable of various threedimensional orientations with respect to the spinal rod. Screws of this type have been referred to as poly-axial or multi-axial bone screws.

Others have approached the solution to this problem with various poly-axial screw designs. For example, in U.S. Pat. No. 5,466,237 to Byrd et al., a bone screw is described which includes a spherical projection on the top of the bone screw. An externally threaded receiver member supports the bone screw and a spinal rod on top of the spherical projection. An outer nut is tightened onto the receiver member to press the spinal rod against the spherical projection to accommodate various angular orientations of the bone screw relative to the rod. While this particular approach utilizes a minimum of components, the security of the fixation of the bone screw to the rod is lacking. In other words, the engagement or fixation between the small spherical projection on the bone screw and the spinal rod is readily disrupted when the instrumentation is subjected to the high loads of the spine, particularly in the lumbar region.

In another approach shown in U.S. Pat. No. 4,946,458 to Harms et al., a spherical headed bone screw is supported within separate halves of a receiver member. The bottom of the halves are held together by a retaining ring. The top of the receiver halves are compressed about the bone screw by nuts threaded onto a threaded spinal rod. In another approach taken by Harms et al., in U.S. Pat. No. , 5,207,678, a receiver member is flexibly connected about a partially spherical head of a bone screw. Conical nuts on opposite sides of the receiver member are threaded onto a threaded rod passing through the receiver. As the conical nuts are threaded toward each other, the receiver member flexibly compresses around the head of the bone screw to clamp the bone screw in its variable angular position. One detriment of the systems in the two Harms et al. patents is that the spinal rod must be threaded in order to accept the compression nuts. It is known that threading rods can tend to weaken the rods in the face of severe spinal loads. Moreover, the design of the bone screws in the '458 and '678 Patents require a multiplicity of parts and are fairly complicated to achieve complete fixation of the bone screw.

A further approach illustrated in U.S. Pat. No. 5,797,911 to Sherman et al., owned by the Assignee of the present invention, is to provide a U-shaped holder through the top of which a bone fastener topped with a crown member is loaded. The holder accommodates a rod in a channel above the crown member and a compression member above the rod. The compression member presses on the rod and crown member to lock the fastener against the holder in any of a number of angles in three dimensions with respect to the rod. This approach has proven to be quite effective in addressing the above-identified problems. However, it does not permit bottom-loading of the fastener. Additionally, the holder is somewhat bulky in order to accommodate the other structural components.

Yet a further approach is shown in U.S. Pat. No. 5,733,285 to Errico et al., in which a holder is provided with a tapered and colletted portion at the bottom into which a bone fastener head is inserted. A sleeve is provided that slides down around the colletted portion to crush lock the colletted portion around the head of the bone fastener. This apparatus is believed to be relatively bulky and difficult to manipulate given the external sliding locking mechanism. It is further dependent on the fit of the external sleeve and the relative strength of the collet and its bending and crushing portions for secure locking of the bone fastener head.

There is therefore a need remaining in the industry for a multi-axial bone anchor that can be readily and securely engaged to an elongated member of any configuration—i.e., smooth, roughened, knurled or even threaded—which achieves improved angulation of the bone anchor, improved strength, and reduced size, including profile and bulk, of the components used to engage the bone anchor to the elongated member in any of a variety of angular orientations.

SUMMARY OF THE INVENTION

In one embodiment of the invention, a bone fixation assembly is provided that includes a receiver member defining an upper opening portion and a lower opening portion, a channel configured to receive an elongated member that communicates with the upper and lower opening portions, and a groove around a portion of the lower opening portion. The assembly further includes a crown member with an upper surface and a lower surface that is movably disposed in the lower opening portion, and a bone-engaging anchor having a lower portion configured to engage a bone and a head smaller than the lower opening portion, with the head being movably disposed in the lower opening portion adjacent to the concave lower surface of the crown member. The assembly also includes a retaining member defining an aperture smaller than the head of the bone anchor that is at least partially housed in the groove of the receiver member and positioned around the bone anchor and below its head.

Additional embodiments, examples, advantages, and objects of the present invention will be apparent to those of ordinary skill in this art from the following specification.

BRIEF DESCRIPTION OF THE DRAWINGS

FIG. 3b is a front elevational view of the embodiment of the receiver member illustrated in FIG. 3a.

FIG. 3c is a sectional view, taken along the lines 3c—3c in FIG. 3a, and viewed in the direction of the arrows, of the embodiment of the receiver member illustrated in FIG. 3a.

FIG. 3d is a sectional view, taken along the lines 3d—3d of FIG. 3b and viewed in the direction of the arrows, of the embodiment of the receiver member illustrated in FIG. 3a.

FIG. 4b is a sectional view, taken along the lines 4b—4b of FIG. 4a and viewed in the direction of the arrows, of the embodiment of the bone anchor illustrated in FIG. 4a.

FIG. 4c is a magnified view of one embodiment of the head of the embodiment of the bone anchor illustrated in FIG. 4a.

FIG. 5b is a sectional view, taken along the lines 5b—5b in FIG. 5a and viewed in the direction of the arrows, of the embodiment of the crown member illustrated in FIG. 5a.

FIG. 6b is a sectional view, taken along the lines of 6b—6b in FIG. 6a and viewed in the direction of the arrows, of the embodiment of the retaining member illustrated in FIG. 6a.

DESCRIPTION OF THE PREFERRED EMBODIMENT

Figures 1, 2:
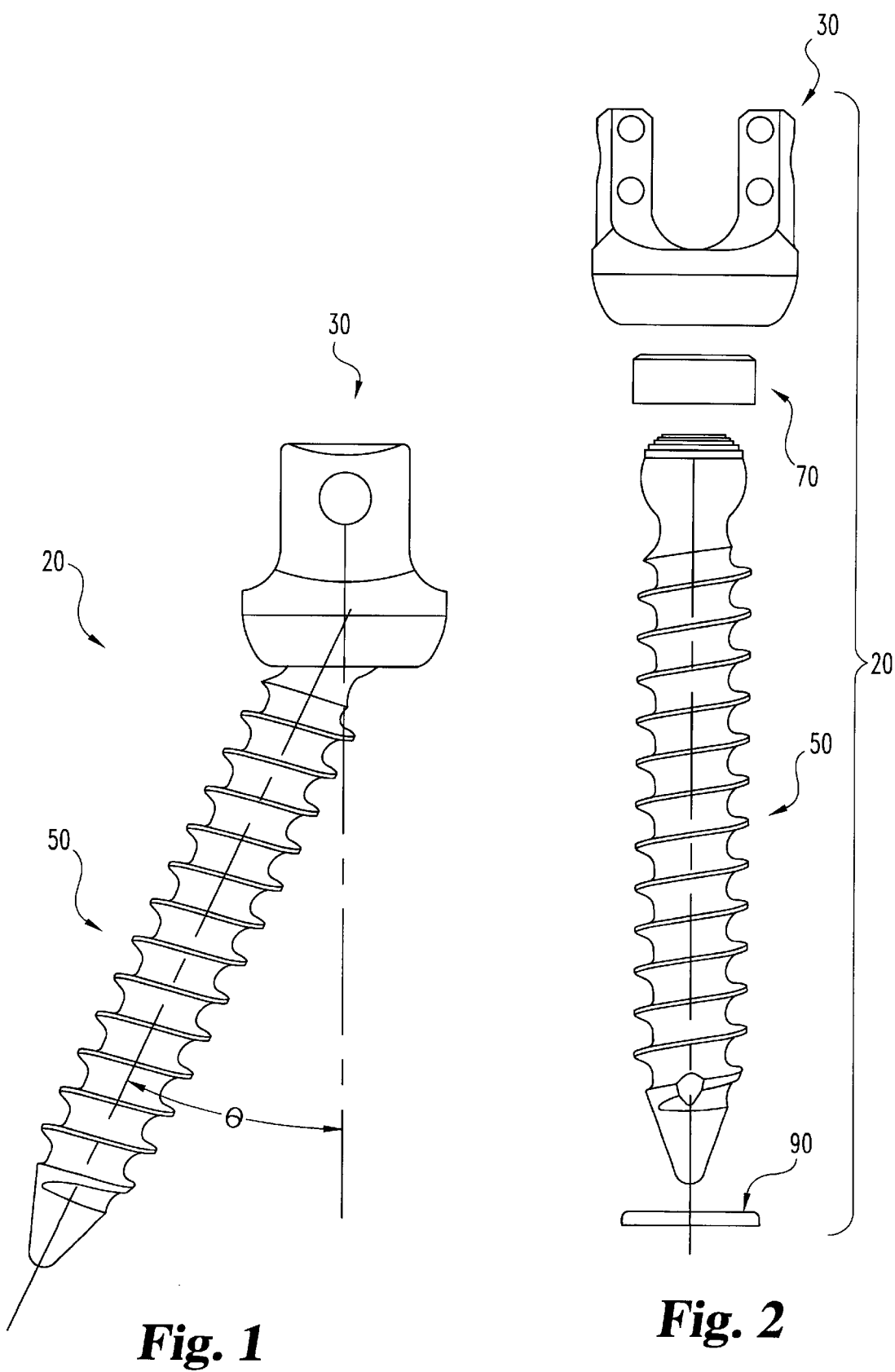
FIG. 1 is a side elevational view of one embodiment of the multi-axial bone screw anchor assembly of the present invention.
FIG. 2 is an exploded view of the embodiment of the invention depicted in FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Referring generally to FIGS. 1 and 2, there is shown one embodiment of a multi-axial bone anchor assembly 20 of the present invention. In the illustrated embodiment, assembly 20 includes a receiver member 30, a bone anchor 50, a crown member 70, and a retaining member 90. The assembly 20 of the present invention is designed for use with an elongated member R (FIG. 7) such as a spinal rod, bar or other orthopedic construct, as further described below.

Referring now generally to FIGS. 3a–3d, one embodiment of the receiver member 30 of the present invention is shown. Receiver member 30 defines an upper opening portion 31a and a lower opening portion 31b, which in the illustrated embodiment form a single opening 32 extending through receiver member 30 from an upper aperture 33 in top end 34 to a lower aperture 35 in bottom end 36. Lower opening portion 31b of opening 32, in one specific embodiment, includes a chamber 38 defined by a chamber wall 39. Alternatively, upper and lower opening portions 31a, 31b can have a variety of configurations, such as each having one or more sections of differing diameter.

Figure 3A:
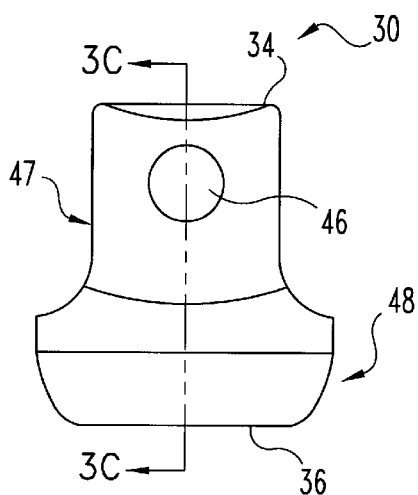
FIG. 3a is a side elevational view of an embodiment of the receiver member of the embodiment of the invention illustrated in FIG. 2.
Figure 3B:
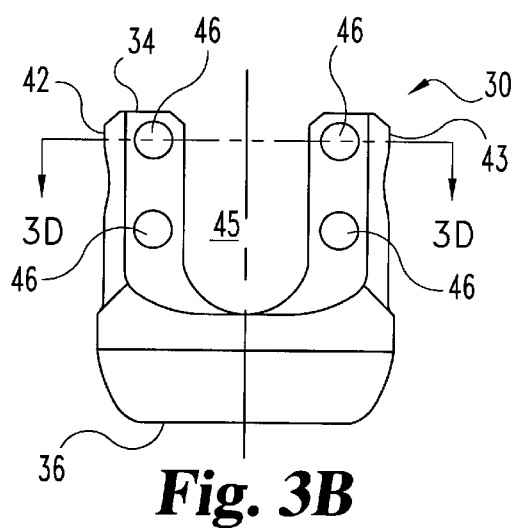
Figure 3C:
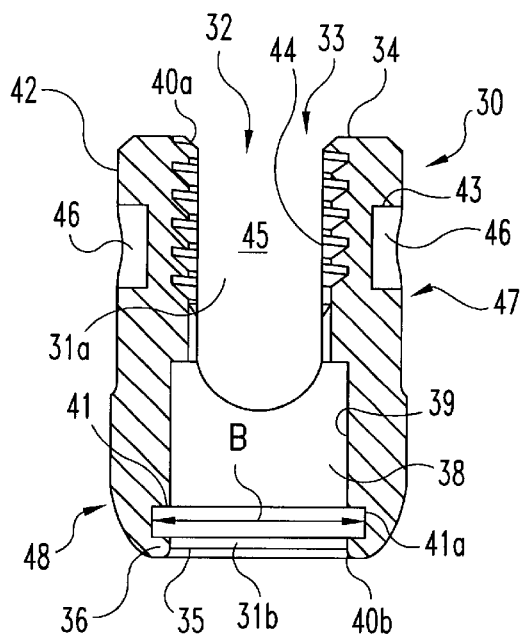
Figure 3D:
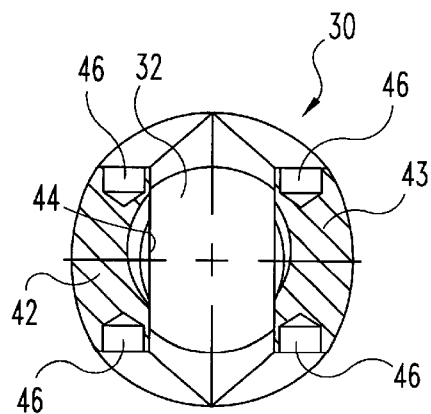

Opening 32 is partially surrounded by a chamfered or rounded edge 40a at top end 34 of receiver member 30, and is surrounded by chamfered or rounded edge 40b at the bottom end 36 of receiver member 30. Proximate to bottom end 36, receiver member 30 defines a groove 41 and associated ledge 41a around opening 32. In the illustrated embodiment, groove 41 extends around the entire perimeter of opening 32, although it will be seen that groove 41 could extend only partially around the perimeter of opening 32. Groove 41 has a groove depth A (FIG. 7) and a groove diameter B (FIG. 3a).

Figure 7:
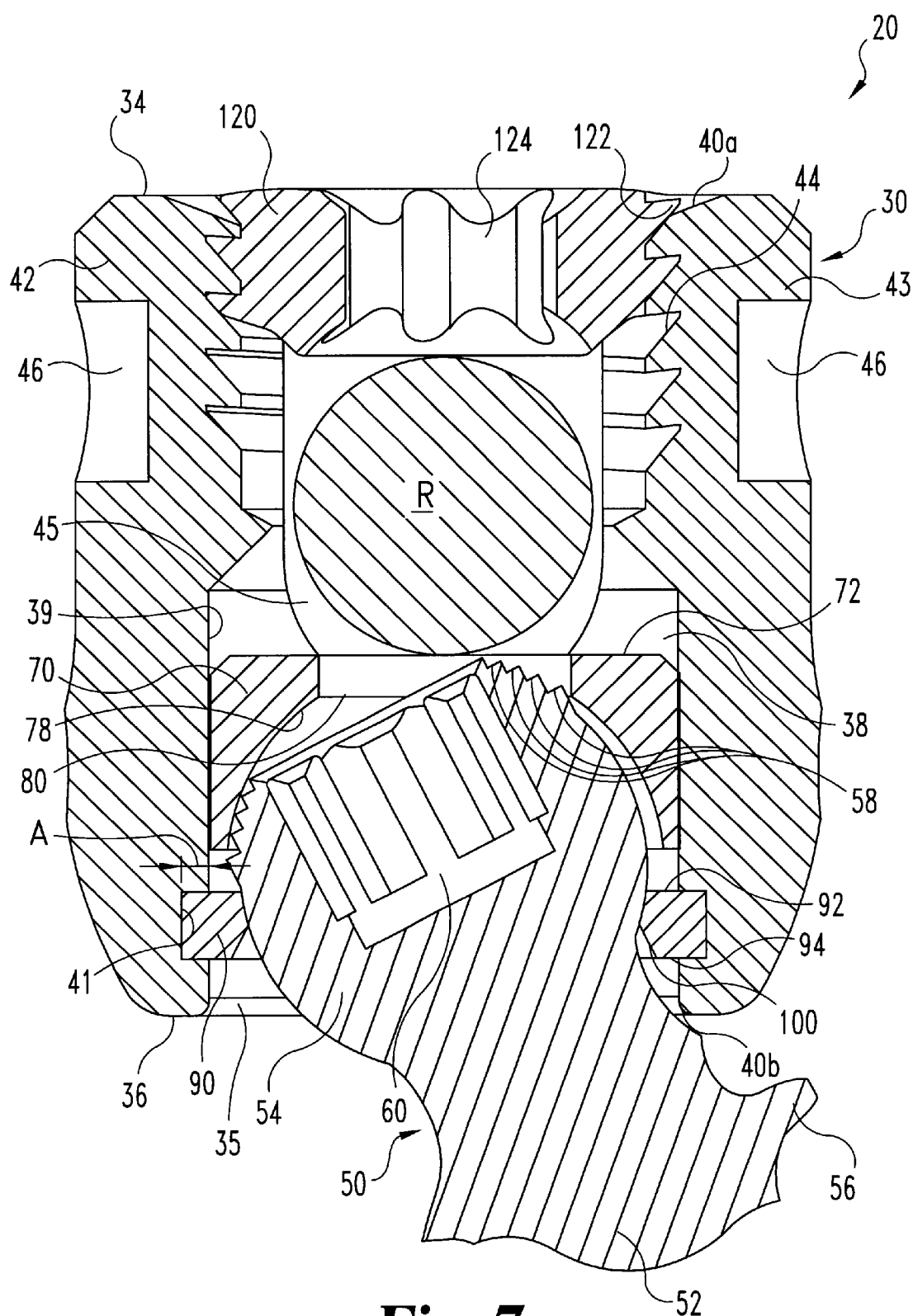
FIG. 7 is an enlarged sectional view of the embodiment of the present invention illustrated in FIG. 1.

Receiver member 30 in the illustrated embodiment includes a pair of upright branches 42, 43 through which opening 32 extends. Branches 42, 43 further define a U-shaped channel 45 transverse to opening 32 that communicates with upper portion 31a and lower portion 31b of opening 32, and that accommodates an elongated member R (FIG. 7). In a specific embodiment, internal threads 44 are formed in branches 42, 43, and branches 42, 43 are provided with indentations or holes 46, which allow the surgeon to grip receiver member 30 with an appropriate tool (not shown). Internal thread 44 in a specific embodiment is a reverse angle thread, i.e. a thread in which the forward face points down and in toward receiver member 30, as disclosed in commonly-owned U.S. patent application Ser. No. 09/188,825, filed Nov. 9, 1998, the disclosure of which is hereby incorporated by reference. Preferably, the top portion 47 of receiver member 30 (which includes branches 42, 43) is narrower than bottom portion 48 of receiver member 30, thereby reducing the bulk and profile of receiver member 30.

Figure 4A:
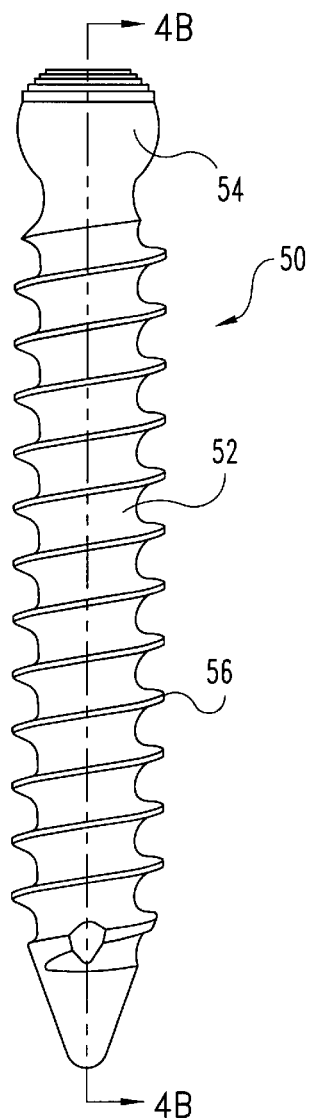
FIG. 4a is a side elevational view of an embodiment of a bone anchor used in the embodiment of the invention illustrated in FIG. 2.
Figure 4B:
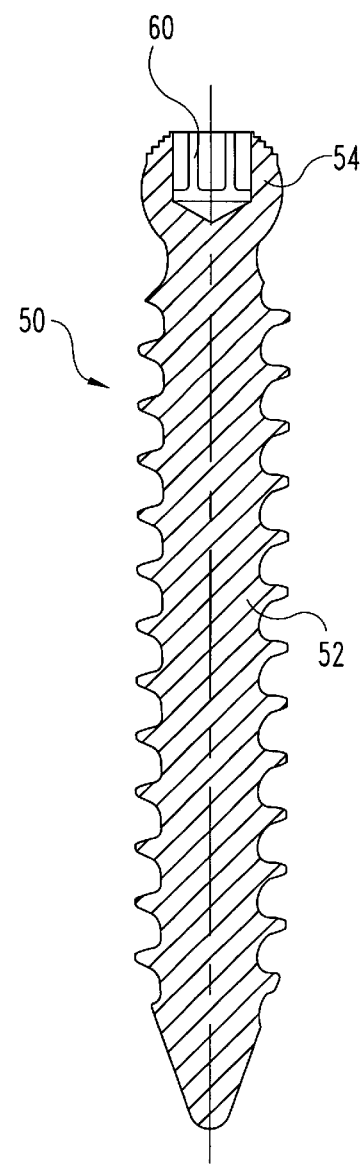
Figure 4C:
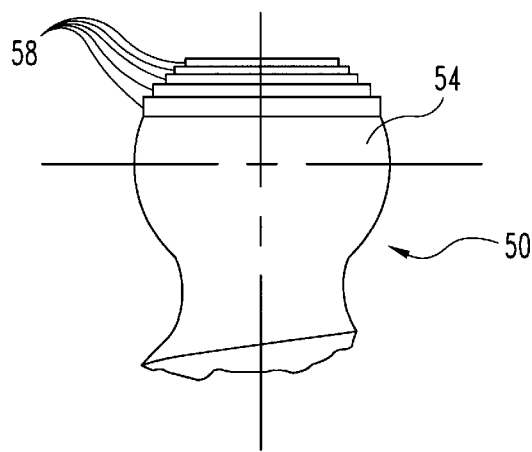

Referring now generally to FIGS. 4a–4c, an embodiment of a bone anchor 50 used in the present invention is shown. The illustrated bone anchor 50 is a bone screw, which in one embodiment is substantially like the bone screw disclosed in U.S. Pat. No. 5,885,286, the disclosure of which patent is hereby incorporated by reference. Bone anchor 50 includes an anchorage portion 52 and a head portion 54. Anchorage portion 52 includes at least one thread 56, which may be a cancellous self-tapping thread. Head portion 54 forms part of a sphere in the illustrated embodiment, though alternative curvate and other configurations may be employed. Head 54 in one particular embodiment includes a series of ridges 58 for improving purchase with the inside of crown member 70 (described below). Head 54 may have alternative friction-increasing surface configuration(s) such as roughening or knurling. Further, head 54 includes a tool-engaging print 60, with which a tool (not shown) may be engaged to drive anchorage portion 52 into a bone. Tool-engaging print 60 is an interior print in the illustrated embodiment, although an exterior print could be used, and it may have any of a number of configurations, such as hexagonal, hexalobate, or other known torque-transferring configurations.

Other embodiments of bone anchor 50 are contemplated as being within the scope of the present invention. For example, bone anchor 50 could be a bone-engaging hook rather than a screw. In that embodiment, anchorage portion 52 would be configured with a hook rather than an elongated section with thread 56.

Head 54 of bone anchor 50 is shaped and sized to fit within at least lower portion 31b of opening 32 and chamber 38 of receiver member 30. Specifically, head 54 has a width that is smaller than the width of lower opening portion 31b and chamber 38. As more fully described below, bone anchor 50 is inserted into receiver member 30, with head 54 entering lower opening portion 31b and chamber 38 through bottom end 36 of receiver member 30.

Figure 5A:
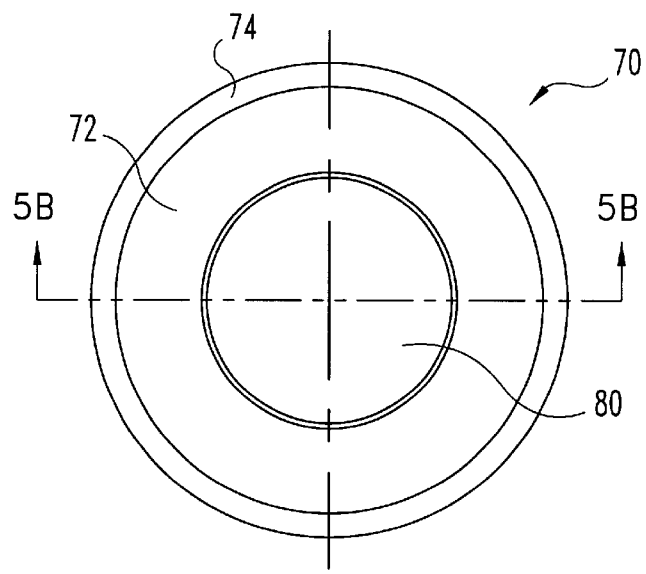
FIG. 5a is a top view of one embodiment of a crown member used in the embodiment of the present invention illustrated in FIG. 2.
Figure 5B:
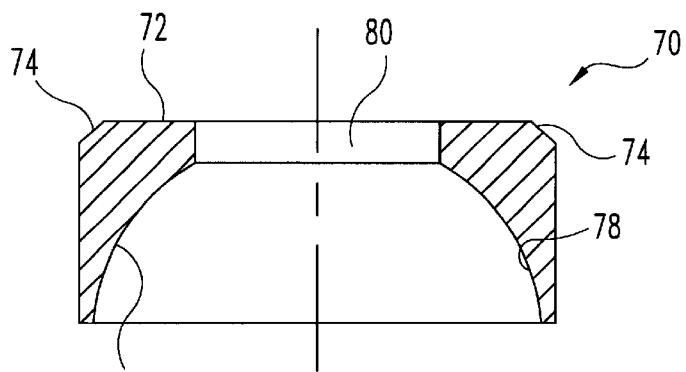
Figure 5C:
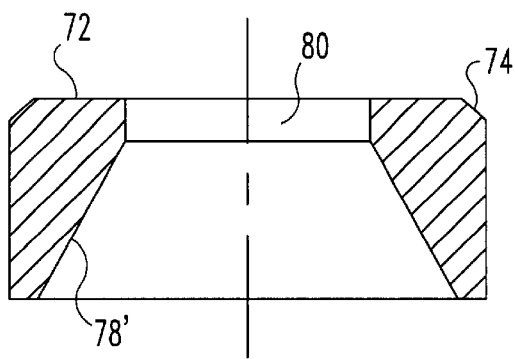
FIG. 5c is a sectional view substantially similar to FIG. 5b of another embodiment of a crown member used in the embodiment of the invention illustrated in FIG. 2.

Referring now to FIGS. 5a–5b, there is shown one embodiment of crown member 70 of the present invention. In that embodiment, crown member 70 is in the shape of a circular disc, having an upper surface 72 with a beveled edge 74 and a lower surface 78. Lower surface 78 is configured to accommodate head 54 of bone anchor 50, and therefore the illustrated embodiment of lower surface 78 has the shape of part of a sphere. Alternatively or additionally, the lower surface of crown member 70 can have one or more other shapes, such as beveled or conical lower surface 78' (FIG. 5c). Lower surface 78 can be provided with a friction- or purchase-enhancing surface configuration (e.g. roughening or knurling) for cooperation with head 54 of bone anchor 50.

The illustrated embodiment of crown member 70 also includes a hole 80. Hole 80 is provided so that head 54, and specifically tool-engaging print 60, of bone anchor 50 may be accessed through crown member 70. Crown member 70 is sized and shaped to fit within at least lower portion 31b of opening 32 and chamber 38 of receiver member 30. The outer dimension of crown member 70 is preferably slightly smaller than the inner dimension of chamber 38 and lower portion 31b of opening 32 so that crown member 70 is slidably and rotatably movable within chamber 38 and opening 32. Further, in the illustrated embodiment the outer dimension of crown member 70 is larger than the inner dimension of upper opening portion 31a, so that crown member 70 cannot move into upper opening portion 31a.

Figure 6A:
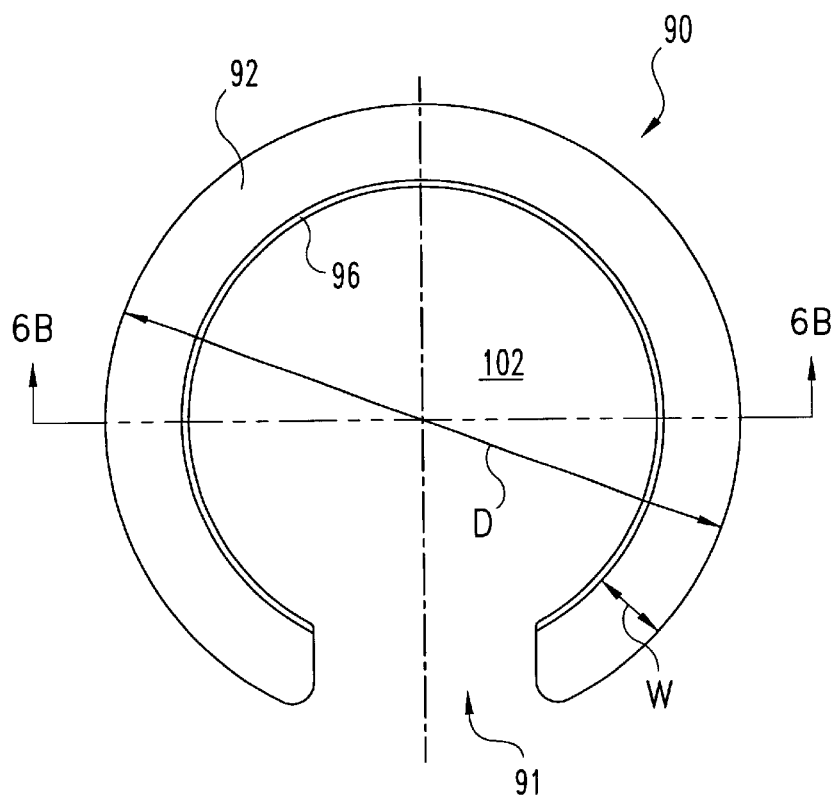
FIG. 6a is a top view of one embodiment of a retaining member used in the embodiment of the invention illustrated in FIG. 2.
Figure 6B:
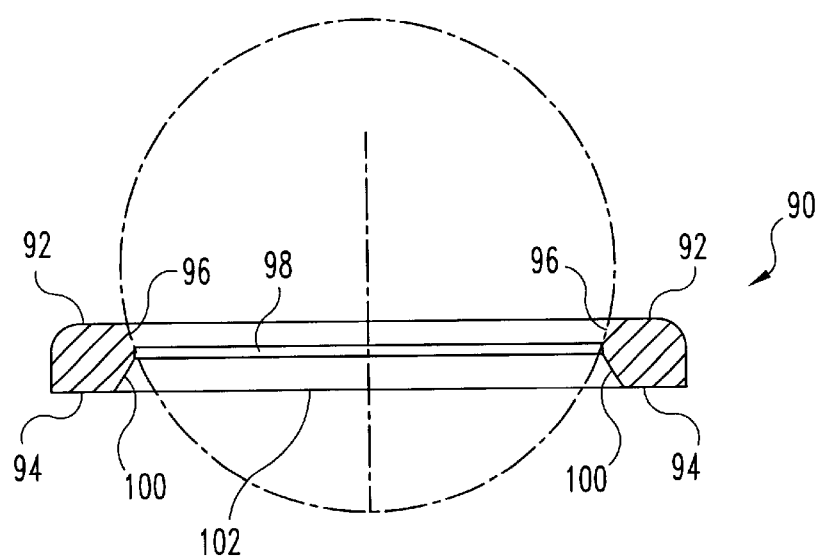

Referring now to FIGS. 6a–6b, there is shown one embodiment of retaining member 90 of the present invention. In the illustrated embodiment, retaining member 90 has the form of a C-shaped spring or clip defining a gap 91. Retaining member 90 includes a top surface 92 and a bottom surface 94. In the illustrated embodiment, retaining member 90 also includes internal surfaces 96, 98, 100 that substantially surround aperture 102. In one specific embodiment, internal surface 96 forms a portion of a sphere of radius substantially identical to the radius of head 54 of bone anchor 50, internal surface 98 is cylindrical, and internal surface 100 is conical and angled outward to allow a greater range of angular positioning of bone anchor 50. In alternative embodiments, there may be single or multiple internal surfaces surrounding aperture 102, which surface(s) may be cylindrical, conical, spherical or of other appropriate configuration. The diameter of aperture 102 is smaller than the diameter of head 54 of bone anchor 50 and the diameter of crown member 70.

Retaining member 90 has an unloaded or natural outer diameter D, i.e. a diameter measured when retaining member 90 is under no contractive (gap-closing) or expansive (gap-opening) stress. Diameter D of retaining member 90, in one embodiment, is less than groove diameter B of groove 41. Further, retaining member 90 has a body width W that is substantially constant throughout retaining member 90. Body width W of retaining member 90 is greater than groove depth A of groove 41.

Generally referring to FIGS. 1, 2 and 7, assembly 20 is assembled as follows: bone anchor 50, crown member 70 and retaining member 90 are inserted into receiver member 30 through bottom end 36, either individually or substantially in one step. For example, crown member 70 may be inserted first, followed by bone anchor 50 with retaining member 90 being inserted last. In one specific embodiment, retaining member 90 is fitted around bone anchor 50 just below head 54 prior to insertion of bone anchor 50 into receiver member 30. Retaining member 90 can be placed around bone anchor 50 by inserting anchorage portion 52 of bone anchor 50 through aperture 102 of retaining member 90 and moving retaining member 90 over anchorage portion 52 toward head 54. Alternatively, gap 91 of retaining member 90 may be pressed against the shank of bone anchor 50 below head 54, so that gap 91 expands to allow placement of bone anchor 50 within aperture 102 of retaining member 90, whereupon retaining member 90 returns to its original size and shape. By placing crown member 70 atop head 54 of bone anchor 50, so that lower surface 78 of crown member 70 adjoins head 54, and fitting bone anchor 50 and retaining member 90 together as described above, simultaneous insertion of bone anchor 50, crown member 70 and retaining member 90 into receiver member 30 can be accomplished.

Crown member 70 remains slideably and rotatably positioned in lower portion 31b of opening 32 and/or chamber 38 of receiving member 30, and bone anchor 50 remains multi-axially moveable with respect to crown member 70 and receiving member 30. Retaining member 90 is forced upward into lower portion 31b of opening 32. Retaining member 90 contracts, making gap 91 smaller, as retaining member 90 is forced against chamfered edge 40b of receiving member 30, until the outer diameter of retaining member 90 is the same as the diameter of lower portion 31b of opening 32. Retaining member 90 is further advanced along opening 32 and into groove 41 so that retaining member 90 is fitted into at least a portion of groove 41.

As noted above, in one specific embodiment the groove diameter B of groove 41 is smaller than the outer diameter D of retaining member 90 in its natural (i.e., unloaded) condition. Thus, when retaining member 90 is within groove 41, retaining member 90 presses against the walls of groove 41. Alternatively, groove diameter B of groove 41 may be the same size or slightly larger than the natural outer diameter D of retaining member 90. In this case, the lower surface 94 of retaining member 90 rests upon ledge 41a of groove 41, and thereby holds retaining member 90 within groove 41. Groove depth A of groove 41 is less than the body width W of retaining member 90, so that when retaining member 90 is fitted in groove 41, a portion of retaining member 90 projects into lower opening portion 31b of opening 32.

When retaining ring 90 is seated within groove 41, bone anchor 50 and crown member 70 are retained within opening 32 of receiver member 30. Crown member 70 is supported by head 54 of bone anchor 50, and head 54 is supported by internal surface 96 of retaining member 90. Retaining member 90 is held by groove 41 and/or ledge 41a of receiver member 30, and thus bone anchor 50 and crown member 70 will not pass through retaining ring 90 and out of receiver member 30 when retaining ring 90 is within groove 41.

Preferably, assembly 20 is assembled (as described above) prior to use in a surgical procedure. In using the illustrated embodiment of assembly 20, bone anchor 50 of assembly 20 is threaded into an appropriately prepared hole in a bone (not shown). It will be understood that in alternative embodiments of the invention, for example where bone anchor 50 is a bone hook, drilling a hole in bone and threading the anchor therein may not be necessary. Threaded anchoring portion 52 is inserted into the hole, and an appropriate screwing tool is used with tool-engaging print 60 of bone anchor 50 through hole 80 in crown member 70, and bone anchor 50 is threaded into the bone. When bone anchor 50 has been threaded into the bone to the desired depth, receiver member 30 is positioned so that opening 32 forms a desired angle with bone anchor 50, as depicted in FIG. 1. In the illustrated embodiment, the angle θ between bone anchor 50 and opening 32 can be any value up to 30 degrees in any direction. It will be seen that the maximum angle of bone anchor 50 relative to opening 32 can be changed in several ways, for example by thinning the portion of bone anchor 50 beneath head 54, by providing steeper angulation of chamfered edge 40b, and/or by placing groove 41 as close as possible to bottom end of 36 of receiver member 30.

As described above, receiver member 30 may be angled as the surgeon desires with respect to bone anchor 50. An elongated member R such as a spinal rod, connector, or other orthopedic surgical implant is coupled with assembly 20. Elongated member R is placed in channel 45 of receiver member 30, and contacts top surface 72 of crown member 70. A compression member 120, such as a set screw or threaded plug, is threaded into threads 44 of receiver member 30 and down onto elongated member R. Compression member 120, in one embodiment, is a set screw or plug having external threads 122 and a print 124 for applying torque, and in a specific embodiment is a break-off set screw as disclosed in U.S. Pat. No. 5,885,286 to Sherman et al., incorporated herein by reference. In a further embodiment, thread 122 is a reverse angle thread as disclosed in U.S. patent application Ser. No. 09/188,825, filed Nov. 9, 1998, incorporated herein by reference, which is compatible with the reverse angle embodiment of thread 44 of receiver member 30, described above. Alternatively, where receiver member 30 is externally threaded, compression member 120 could be an internally-threaded nut.

As compression member 120 is tightened, elongated member R is forced downward against crown member 70, which pushes crown member 70 down onto head 54 of bone anchor 50. Head 54 is thereby clamped between retaining member 90 and crown member 70. In the embodiment of the invention in which head 54 includes ridges 58, ridges 58 are pressed into lower surface 78 of crown member 70. In this way, bone anchor 50 is locked into the desired angular position with respect to elongated member R and the remainder of assembly 20.

Alternatively, assembly 20 can be assembled during the surgical procedure. Bone anchor 50, with retaining ring 90 already positioned beneath head 54, is inserted into the bone. Crown member 70 is placed atop bone anchor 50 or in opening 32 in receiver member 30. Receiver member 30 is then pressed down onto head 54 of bone anchor 50, forcing retaining ring 90 to contract, to enter opening 32, and to seat in groove 41 as described above. After assembly 20 is assembled in this fashion, an elongated member is loaded into receiver member 30 and locked as previously described.

Preferred materials for the present invention include stainless steel and titanium. It will be recognized that any sturdy biocompatible material may be used to accomplish the osteosynthesis and other orthopedic surgical goals of the present invention. In one specific embodiment, crown member 70 may be made of a material somewhat softer than the material used for ridges 58 of head 54 of bone anchor 50. Such construction will allow ridges 58 to penetrate somewhat more easily into interior surface 78 of crown member 70 during locking of assembly 20, thereby providing a more definite purchase between ridges 58 and crown member 70. In another specific embodiment, crown member 70 may be made of a material somewhat softer than the material used for elongated member R. Such construction will allow upper surface 72 of crown member 70 to deform to the shape of elongated member R during locking of assembly 20, also providing a more secure locking of the implant.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A bone anchor assembly for engagement to an elongated member, comprising:
   a receiver member defining an upper opening portion and a lower opening portion each having respective minimum widths, a channel configured to receive the elongated member and communicating with said upper opening portion and said lower opening portion, and a groove around a portion of said lower opening portion;
   a crown member movably disposed in said lower opening portion, said crown member including an upper surface and a lower surface;
   a bone-engaging anchor having a lower portion configured to engage a bone and a head having a width, said width of said head being smaller than said minimum width of said lower opening portion, said head being movably disposed in said lower opening portion adjacent to said lower surface of said crown member; and
   a retaining member defining an aperture smaller than said width of said head, said retaining member at least partially housed in said groove of said receiver member and positioned around said anchor and below said head,
   wherein said retaining member prevents removal of said head from said lower opening portion.

2. The assembly of claim 1, wherein said upper opening portion and said lower opening portion form at least part of a single opening through said receiver member.

3. The assembly of claim 2, wherein said receiver member includes two branches which define said upper opening portion and said channel.

4. The assembly of claim 3, wherein said branches include internal threads.

5. The assembly of claim 4 further including a compression member threadedly connected to said internal threads.

6. The assembly of claim 2, wherein said receiver member defines a chamber that forms at least a part of said lower opening portion, and said crown member being movably disposed within said chamber.

7. The assembly of claim 6, wherein said anchor is a bone screw.

8. The assembly of claim 7, wherein said head of said bone screw is at least partially spherical.

9. The assembly of claim 8, wherein said head of said bone screw includes ridges.

10. The assembly of claim 8, wherein said lower surface of said crown member is at least partially spherical.

11. The assembly of claim 10, wherein said lower surface of said crown member includes a roughened portion.

12. The assembly of claim 6, wherein said crown member has a width greater than said upper opening portion of said receiver member.

13. The assembly of claim 12, wherein said head of said bone anchor includes a tool-engaging print.

14. The assembly of claim 13, wherein said crown member defines a hole through said upper surface through which said head of said bone anchor can be accessed.

15. The assembly of claim 12, wherein said retaining member is a C-shaped member.

16. The assembly of claim 15, wherein said retaining member has an unloaded outer diameter, said receiver member has a groove diameter, and said unloaded outer diameter of said retaining member is greater than said groove diameter of said receiver member.

17. The assembly of claim 16, wherein said retaining member has a body width, said groove has a groove depth, and said body width is greater than said groove depth.

18. The assembly of claim 17, wherein said retaining member includes an inner concave surface for engaging said head of said bone anchor.

19. The assembly of claim 18, wherein said inner concave surface forms part of a sphere.

20. The assembly of claim 2, wherein said lower surface of said crown member is beveled.

21. The assembly of claim 2, wherein said lower surface of said crown member is concave.

22. The assembly of claim 2, wherein said crown member has a width greater than said upper opening portion of said receiver member.

23. The assembly of claim 22, wherein said crown member defines a hole through said upper surface through which said head of said bone anchor can be accessed.

24. The assembly of claim 2, wherein said retaining member is a C-shaped member.

25. The assembly of claim 24, wherein said retaining member has an unloaded outer diameter, said receiver member has a groove diameter, and said unloaded outer diameter of said retaining member is greater than said groove diameter of said receiver member.

26. The assembly of claim 24, wherein said retaining member has a body width, said groove has a groove depth, and said body width is greater than said groove depth.

27. The assembly of claim 26, wherein said retaining member includes an inner concave surface for engaging said head of said bone anchor.

28. The assembly of claim 27, wherein said inner concave surface forms part of a sphere.

29. A bone fixation apparatus comprising:
   an elongated member configured for placement adjacent and along a length of at least one bone;
   a receiver member defining an opening therethrough from a top end to a bottom end, said opening having a lower aperture at said bottom end and an upper aperture at said top end, said receiver member also defining a groove around a portion of said opening, said groove being proximate to said lower aperture, said receiver member further including a channel communicating with said opening and said upper aperture, said channel being configured to receive said elongated member therein;
   a crown member insertable through said lower aperture and disposed within said opening, said crown member having a lower surface and an opposite upper surface contacting said elongated member;
   a bone anchor having a lower portion configured for engaging a bone and a head having a width dimension, said head being insertable through said lower aperture and adjacent to said crown member within said opening of said receiver member;
   a retaining member defining an aperture having a width dimension that is less than said width dimension of said head, said retaining member being positioned around a portion of said bone anchor and at least a portion of said retaining member being housed within at least a portion of said groove; and
   a compression member engaged within said opening proximate to said upper aperture, said compression member operable to press said elongated member against said crown member, thereby fixing said head of said fastener between said crown member and said retaining member.

30. The apparatus of claim 29, wherein said elongated member is a spinal rod.

31. The apparatus of claim 29, wherein said retaining member is a C-shaped member.

32. The apparatus of claim 31, wherein said retaining member has an unloaded outer diameter, said receiver member has a groove diameter, and said unloaded outer diameter of said retaining member is greater than said groove diameter of said receiver member.

33. The apparatus of claim 32, wherein said retaining member has a body width, said groove has a groove depth, and said body width is greater than said groove depth.

34. The apparatus of claim 33, wherein said retaining member includes an inner concave surface for engaging said head of said bone anchor.

35. The apparatus of claim 34, wherein said inner concave surface forms part of a sphere.

36. The apparatus of claim 29, wherein said crown member defines a hole through said upper surface through which said head of said bone anchor can be accessed.

37. The apparatus of claim 29, wherein said head of said bone anchor is at least partially spherical.

38. The apparatus of claim 37, wherein said lower surface of said crown member is at least partially spherical.

39. An apparatus for receiving and holding components of a multi-axial bone anchor system, comprising a member defining an upper opening portion and a lower opening portion, a channel transverse to and communicating with said upper opening portion and said lower opening portion, and a groove around at least a portion of said lower opening portion.

40. The apparatus of claim 39, wherein said upper opening portion and said lower opening portion form at least part of an opening through said member from a top end to a bottom end.

41. The apparatus of claim 39, wherein said groove is proximate said bottom end of said member.

42. The apparatus of claim 40, wherein at least a portion of said upper opening portion is threaded.

43. The apparatus of claim 41, wherein said member includes two branches that define said upper opening portion and at least a portion of said channel.

* * * * *